(12) United States Patent
Yang

(10) Patent No.: US 6,554,841 B1
(45) Date of Patent: Apr. 29, 2003

(54) STRIPED SLEEVE FOR STENT DELIVERY

(75) Inventor: Dachuan Yang, Plymouth, MN (US)

(73) Assignee: SciMed Life Systems, Inc., Maple Grove, MN (US)

(*) Notice: Subject to any disclaimer, the term of this patent is extended or adjusted under 35 U.S.C. 154(b) by 69 days.

(21) Appl. No.: 09/668,496

(22) Filed: Sep. 22, 2000

(51) Int. Cl.⁷ ............................................. A61F 11/00
(52) U.S. Cl. ..................... 606/108; 623/1.11; 606/194
(58) Field of Search .................. 623/1.11, 1.12; 606/108, 191, 192, 194, 195; 604/103.03, 103.05, 171, 180, 263, 264, 523–527

(56) References Cited

U.S. PATENT DOCUMENTS

| | | | |
|---|---|---|---|
| 3,825,036 A | 7/1974 | Stent | 138/174 |
| 4,187,390 A | 2/1980 | Gore | 174/102 |
| 4,877,661 A | 10/1989 | House et al. | 428/34.9 |
| 4,950,227 A | 8/1990 | Savin et al. | 604/8 |
| 5,026,513 A | 6/1991 | House et al. | 264/127 |
| 5,108,416 A | 4/1992 | Ryan et al. | 606/194 |
| 5,403,341 A | 4/1995 | Solar | 606/198 |
| 5,456,674 A | 10/1995 | Bos et al. | 604/280 |
| 5,643,278 A | 7/1997 | Wijay | 606/108 |
| 5,662,703 A | 9/1997 | Yurek et al. | 623/1 |
| 5,670,558 A | 9/1997 | Onichi et al. | 523/112 |
| 5,749,851 A | 5/1998 | Wang | 604/96 |
| 5,752,934 A | 5/1998 | Campbell et al. | 604/96 |
| 5,788,707 A | 8/1998 | Del Toro et al. | 606/108 |
| 5,810,871 A | 9/1998 | Tuckey et al. | 606/198 |
| 5,836,965 A | 11/1998 | Jendersee et al. | 606/198 |
| 5,843,116 A | 12/1998 | Crocker et al. | 606/192 |
| 5,902,631 A | 5/1999 | Wang et al. | 427/2.1 |
| 5,935,135 A | 8/1999 | Bramfitt et al. | 606/108 |
| 5,944,726 A | 8/1999 | Blaeser et al. | 606/108 |
| 5,968,069 A | 10/1999 | Dusbabek et al. | 606/194 |
| 5,976,120 A | 11/1999 | Chow et al. | 604/525 |
| 6,059,813 A | 5/2000 | Vrba et al. | 606/198 |
| 6,068,634 A * | 5/2000 | Lorentzen Cornelius et al. | 606/198 |
| 6,183,505 B1 | 2/2001 | Mohn, Jr. et al. | 623/1.11 |
| 6,331,186 B1 * | 12/2001 | Wang et al. | 623/1.11 |
| 6,387,118 B1 * | 5/2002 | Hanson | 623/1.11 |

OTHER PUBLICATIONS

U.S. patent application Ser. No. 09/664,267, F. Dicaprio et al., filed Sep. 18, 2000.
U.S. patent application Ser. No. 09/664,268, Scott Hanson, filed Sep. 18, 2000.
U.S. patent application Ser. No. 09/407,836, Wang et al., filed Sep. 28, 1999.

* cited by examiner

*Primary Examiner*—David J. Isabella
*Assistant Examiner*—Urmi Chattopadhyay
(74) *Attorney, Agent, or Firm*—Vidas, Arrett & Steinkraus, P.A.

(57) ABSTRACT

A stent delivery system comprising a catheter. The catheter including a stent mounting region and a stent disposed thereabout. The stent having a distal end and a proximal end, and an unexpanded state and an expanded state. At least one stent retaining sleeve, having a first end and a second end, wherein the first end overlays an end of the stent when the stent is in the unexpanded state. The second end engaged to at least a portion of the catheter adjacent to the stent mounting region. The at least one stent retaining sleeve comprising a first material and at least one substantially longitudinally oriented stripe of a second material. The first material having a predetermined hardness and the second material having a predetermined hardness wherein the predetermined hardness of the second material has a greater Shore durometer value than the predetermined hardness of the first material.

20 Claims, 4 Drawing Sheets

STRIPED SLEEVE FOR STENT DELIVERY

CROSS-REFERENCE TO RELATED APPLICATIONS

Not Applicable

STATEMENT REGARDING FEDERALLY SPONSORED RESEARCH

Not Applicable

BACKGROUND OF THE INVENTION

1. Field of the Invention

This invention relates to medical device delivery catheters in general, and specifically to balloon catheters for use in delivering a medical device such as a stent to a desired body location, such as in a blood vessel. More specifically, this invention relates to a stent retaining sock or sleeve composed of a generally elastic material, but which also includes at least one substantially longitudinally oriented stripe of relatively hard or inflexible material therewith. The unique configuration of the different sleeve materials provides for a sleeve which when mounted on a stent delivery balloon catheter may expand, at the end overlapping the stent, to up to 400 percent or more than its unexpanded diameter when the balloon is expanded for stent delivery. However, because of the configuration of the sleeve materials, the end of the sleeve engaged to the catheter experiences minimal or no expansion.

2. Description of the Related Art

Stents and stent delivery assemblies are utilized in a number of medical procedures and situations, and as such their structure and function are well known. A stent is a generally cylindrical prosthesis introduced via a catheter into a lumen of a body vessel in a configuration having a generally reduced diameter and then expanded to the diameter of the vessel. In its expanded configuration, the stent supports and reinforces the vessel walls while maintaining the vessel in an open, unobstructed condition.

Both self-expanding and inflation expandable stents are well known and widely available in a variety of designs and configurations. Self-expanding stents must be maintained under positive external pressure in order to maintain their reduced diameter configuration during delivery of the stent to its deployment site. Inflation expandable stents may be crimped to their reduced diameter about the delivery catheter, maneuvered to the deployment site, and expanded to the vessel diameter by fluid inflation of a balloon positioned on the delivery catheter. The present invention is particularly concerned with delivery and deployment of inflation expandable stents, although it is generally applicable to self-expanding stents when used with balloon catheters.

In advancing an inflation expandable stent through a body vessel to the deployment site, there are a number of important considerations. The stent must be able to securely maintain its axial position on the delivery catheter, without translocating proximally or distally, and especially without becoming separated from the catheter. The stent, particularly its distal and proximal ends, must be protected to prevent distortion of the stent and to prevent abrasion and/or reduce trauma of the vessel walls.

Inflation expandable stent delivery and deployment assemblies are known which utilize restraining means that overlie the stent during delivery. U.S. Pat. No. 4,950,227 to Savin et al, relates to an expandable stent delivery system in which a sleeve overlaps the distal or proximal margin (or both) of the stent during delivery. That patent discloses a stent delivery system in which a catheter carries, on its distal end portion, a stent which is held in place around the catheter prior to and during percutaneous delivery by means of one and preferably two sleeves. The sleeves are positioned around the catheter with one end portion attached thereto and overlap an end portion(s)-of the stent to hold it in place on the catheter in a contracted condition. Each sleeve is elastomeric in nature so as to stretch and release the stent when it expands for implantation. The stent is expandable by means of the expandable balloon on the catheter. During expansion of the stent at the deployment site, the stent margins are freed of the protective sleeve(s). U.S. Pat. No. 5,403,341 to Solar, relates to a stent delivery and deployment assembly which uses retaining sheaths positioned about opposite ends of the compressed stent. The retaining sheaths of Solar are adapted to tear under pressure as the stent is radially expanded, thus releasing the stent from engagement with the sheaths. U.S. Pat. No. 5,108,416 to Ryan et al., describes a stent introducer system which uses one or two flexible end caps and an annular socket surrounding the balloon to position the stent during introduction to the deployment site.

Copending U.S. patent application Ser. No. 09/407,836 which was filed on Sep. 28, 1999 and entitled *Stent Securement Sleeves and Optional Coatings and Methods of Use*, and which is incorporated in its entirety herein by reference, also provides for a stent delivery system having sleeves. In Ser. No. 09/407,836 the sleeves may be made up of a combination of polytetrafluoroethylene (PTFE) as well as one or more thermoplastic elastomers. Other references exist which disclose a variety of stent retaining sleeves.

The entire content of all patents and applications listed within the present patent application are incorporated herein by reference.

BRIEF SUMMARY OF THE INVENTION

In at least one embodiment, the instant invention is directed to a medical device delivery system comprising a catheter assembly having a medical device receiving region and at least one retaining sleeve for retaining the medical device on the receiving region prior to delivery. An expandable medical device, such as a stent, is disposed about the medical device receiving region of the catheter assembly. At least one retaining sleeve is disposed about an end of the expandable medical device and at least a portion of the catheter assembly.

The at least one retaining sleeve further comprises a first material and a second material. The first and second materials having different hardnesses, the second material being harder than the first. As is known, for most polymer materials, the hardness represents the capacity of elongation when the polymer is exposed to an outside acting force, this is especially true for elastomeric materials (e.g. the lower a material's hardness the higher the material's elasticity). The first material generally comprises the tubular body of the at least one retaining sleeve whereas the second material comprises a substantially longitudinally oriented stripe therewith.

BRIEF DESCRIPTION OF THE SEVERAL VIEWS OF THE DRAWINGS

A detailed description of the invention is hereafter described with specific reference being made to the drawings in which.

DETAILED DESCRIPTION OF THE INVENTION

Figure 1:
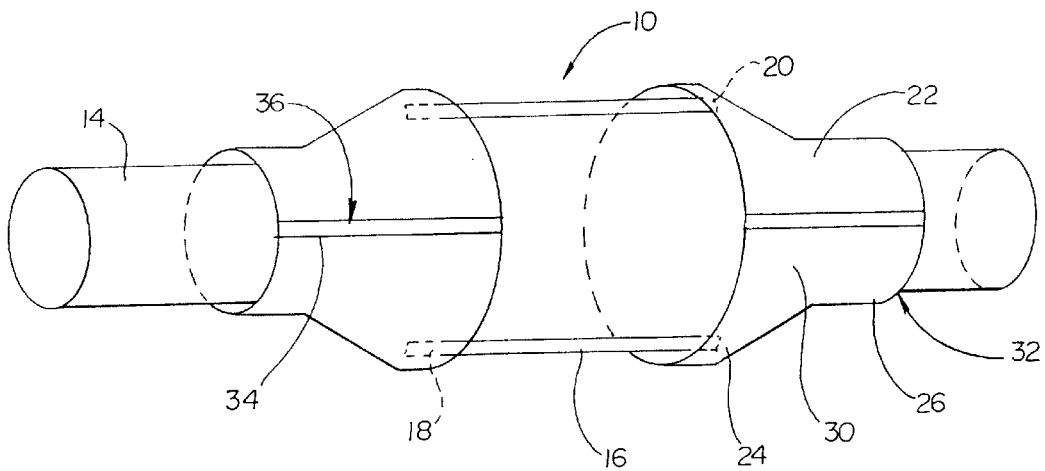
FIG. 1 is a perspective view of an embodiment of the invention.

As may be seen in FIG. 1, the present invention may be embodied in a stent delivery catheter, indicated generally at 10. Catheter 10, includes a stent mounting region 12, the stent mounting region 12 may be an inflatable portion of the catheter or may be a separate balloon mounted to the catheter shaft 14. The balloon 12 may have an unexpanded state and an expanded state. A stent 16, disposed about the stent mounting region 12 may be delivered when the balloon 12 is expanded to the expanded state.

The stent 16 includes a proximal end 18 and a distal end 20. In the embodiment shown a stent retaining sleeve 22 overlies at least a portion of each end 18 and 20. As is known in the art, when the balloon 12 and stent 16 are expanded to their expanded state, the ends of the stent retaining sleeves will often likewise expand and may also be configured to retract off of the stent ends. In the present invention, the sleeves 22 have a unique construction which allows a first portion 24 of the sleeve which overlies the stent 16 to attain a radial expansion of up to 400 percent. The second portion 26 of the sleeve 22 is disposed about and is engaged to a portion of the catheter shaft 14 adjacent to the balloon 12. Because the second portion 26 is not typically subjected to an expansive force its radial expansion is minimal. When the sleeve is expanded, the sleeve undergoes minimal or no increase in length.

As stent 16 is expanded, the stent ends 18 and 20 will eventually be drawn from underneath the stent retaining sleeves 22 by manner of the longitudinal reduction of the stent which occurs during stent expansion relative to the sleeves 22. The present sleeves 22 may expand to nearly the same extent as the balloon 12 and remain engaged to ends 18 and 20 thereby ensuring the position of the stent 16 on the catheter 14. By providing a sleeve 22 which may control the time of the release of the stent 16 during the expansion procedure, the present invention ensures that the stent is delivered in an extremely accurate and consistent manner.

The sleeves 22 are capable of expanding in the manner described as a result of their unique construction. As previously indicated, the sleeves 22 are constructed from at least two materials having different hardness characteristics. The first material 30 is formed into a generally tubular body 32 which provides the sleeve with its shape. The second material 34 is embodied in at least one substantially longitudinally oriented stripe 36.

The first material may be any elastic material known which has a hardness as measured by a Shore durometer of less than 40D. Preferably the durometer hardness of the first material is between 40A and 100A. The second material 34 may be any material having a durometer hardness between about 40D and 75D.

Because the stripe 36 extends substantially across the longitudinal length of the sleeve 22, the harder material 34 will tend to provide a greater restriction on longitudinal expansion compared to radial expansion of the sleeve as has been previously described.

The first material 30 may be selected from one or more of the following substances: polyurethane-polyether polymers, such as Tecothane™ 1074A available from Thermedics, Inc.; polyester-polyurethanes, such as Pellethane™ 2103-70A sold by Dow Chemical; polyether-polyurethanes, such as Estane™ 5703P sold by BF Goodrich; polyether. block amides, such as Pebax™ 2533 available from Elf Atochem; and styrene-butadienstyrene triblock copolymers such as Kraton™ D1101 sold by Shell Chemical company. Other materials which may also be used in the production of the first material 30 include, but are not limited to styrenic block copolymers, polyurethanes, silicone rubber, natural rubber, copolyesters, polyamides, EPDM rubber/polyolefin, nitril rubber/PVC, fluoroelastomers, butyl rubber, epichlorohydrin, and any combinations thereof.

The second material 34 may be selected from one or more of the following substances: polyurethane-polyether polymers, such as Tecothane™ 1055D or 1065D both of which are available from Thermedics, Inc.; polyether-polyurethanes, such as Estane™ 58237 sold by BF Goodrich; polyether block amides, such as Pebax™ 7233 or 6333 both of which are availible from Elf Atochem. Other materials which may also be used in the production of the second material 34 include, but are not limited to: polyolefins, polystyrene, polyvinyl chloride, acrylonitrile-butadiene-styrene polymers, polyacrylonitrile, polyacrylate, vinyl acetate polymer, cellulose plastics, polyurethanes, polyethylene terephthalate, polyacetal, polyethers, polycarbonates, polyamides, polyphenylene sulfide, polyarylethersulfones, polyarylethersketones, polytetrafluoroethylene, and any combinations thereof.

The above examples of the first and second materials 30 and 34 are in no way exhaustive of the potential substances or combinations of substances which may be used. The present invention is directed to a sleeve composed of any materials which have the hardness qualities previously described for the respective materials 30 and 34.

As may be seen in the various figures, the present invention may be embodied in a variety of manners. For instance, in the embodiment shown in FIG. 1 the catheter 10 is seen with a pair of sleeves 22 each of which have a single longitudinally parallel stripe 36. The stripe 36 may be a coating of second material 34 applied to the surface of the body 32. Alternatively, the material 34 of stripe 36 may be bonded or welded to the material 30 of the body 22, or the materials 30 and 34 may have been coextruded together in the form of sleeve. shown. Other methods for joining the materials 30 and 34, such as coating or printing (selectively coating), may also be utilized.

Figure 2:
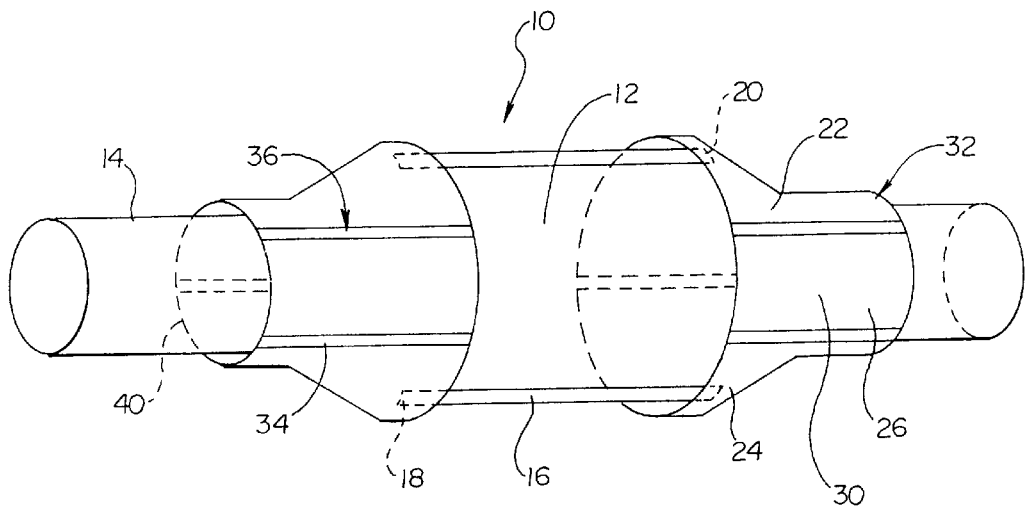
FIG. 2 is a perspective view of an embodiment of the invention.

As may be seen in FIG. 2, the sleeve(s) 22 may include a plurality of stripes. The stripes 36 may be arranged in any manner desired, for example, the stripes 36 may be positioned in a uniform manner relative to one another about the circumference 40 of the sleeve 22.

Figure 3:
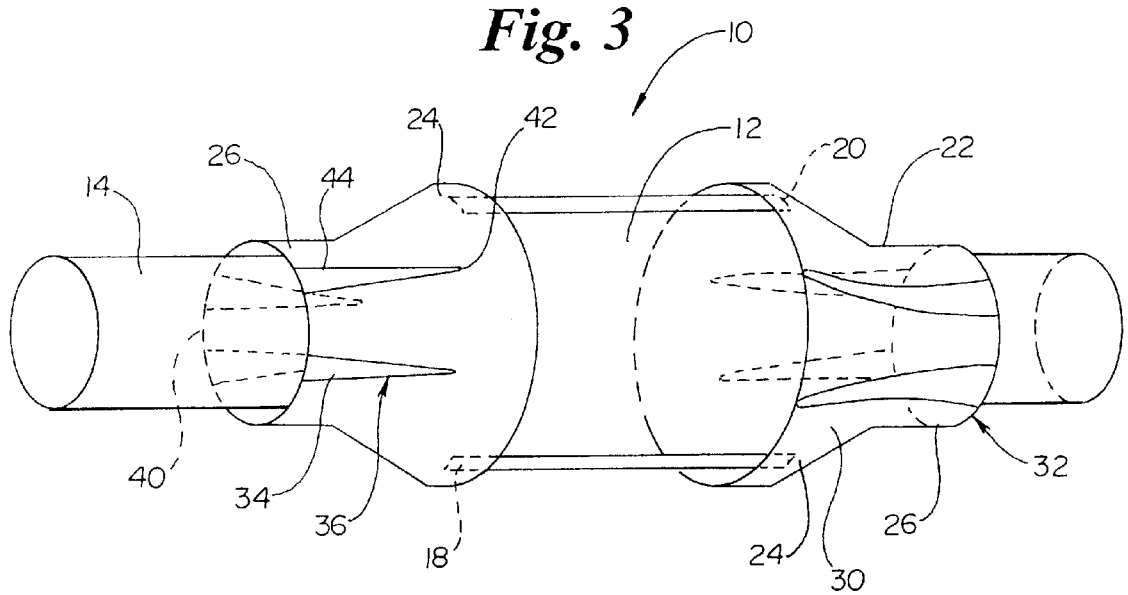
FIG. 3 is a perspective view of an embodiment of the invention.

In FIG. 3 an embodiment of the invention is shown wherein the sleeves 22 have stripes 36 which are tapered. Each stripe 36 has a first end 42 and a second end 44. The first end corresponds to the portion 24 of the sleeve 22 which overlies the end of the stent 16 and the second end 44 corresponds to the portion 26 of the sleeve 22 which is engaged to the catheter shaft 14. The second end 44 has a predetermined width which is greater than and tapers to the predetermined width of the first end 42. By providing the portion 26 of the sleeve 22 with a proportionally harder second material 34 than the first portion 24, the second portion will have a greater resistance to expansion and will therefor remain engaged to the shaft 14 through out most of the stent delivery procedure. At the same time the comparatively reduced amount of second material 34 at or near the first portion of the sleeve 22, will allow the first portion 24 to more readily and fully expand according to the expansion characteristics of the first material 30, as previously described.

Figure 4:
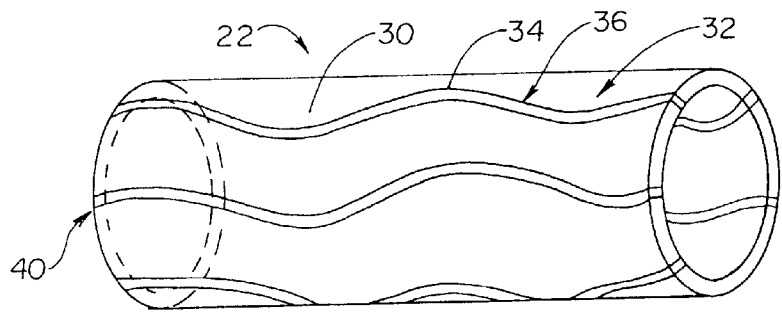
FIG. 4 is a perspective view of an embodiment of the invention.
Figure 5:
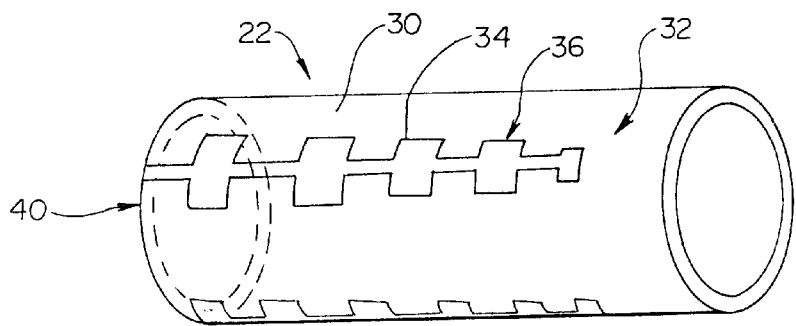
FIG. 5 is a perspective view of an embodiment of the invention.
Figure 6:
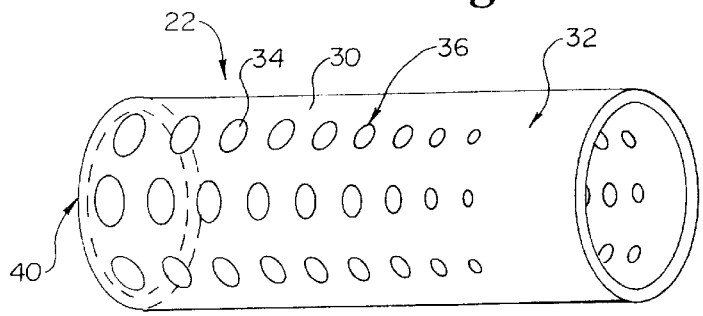
FIG. 6 is a perspective view of an embodiment of the invention.

FIGS. 4–6 show additional configurations of the stripe 36 as it may be embodied on a sleeve 22 design. FIG. 4 shows a sleeve 22 which includes a plurality of stripes 36 having a sinusoidal configuration. FIG. 5, shows a stripe 36 having a patterned configuration. The present pattern provides a concentration of harder second material 34 near the second portion of the sleeve 26, in a manner similar to that of the tapered sleeve shown in FIG. 3. In FIG. 6 the sleeve 22 includes stripes 36 which are intermittent. The stripes 36 are in effect a predetermined arrangement of hardened points of material 34. The material 34 may be arranged in a wide variety of patterns. For example, any of the embodiments of stripes 36 described herein could be presented in an intermittent fashion. Other arrangements may also be provided.

As previously discussed the stripes 36 may be applied to or combined with the body 32 in a variety of manners. For instance where the second material 34 is a coating, the stripe(s) 36 may be directly applied to a surface of the sleeve 22, in any of the patterns or configurations discussed thus far. In the embodiments shown in FIGS. 7–12 a variety of additional stripe 36 and body 32 arrangements are shown.

Figure 7:
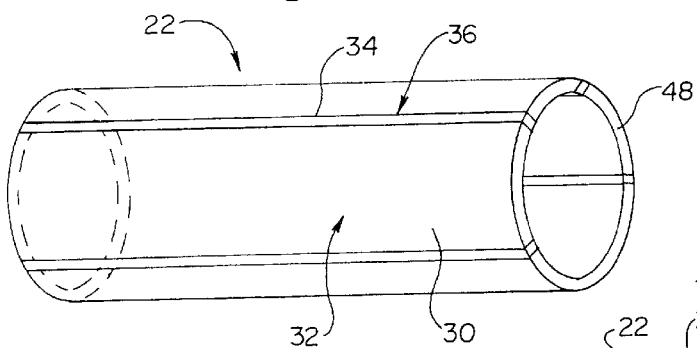
FIG. 7 is a perspective view of an embodiment of the invention.
Figure 8:
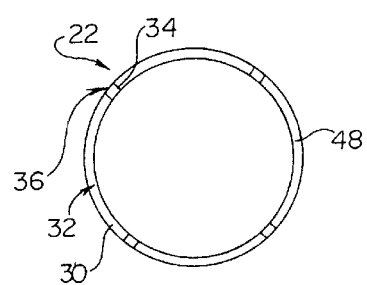
FIG. 8 is a cross-sectional view of the embodiment of the invention shown in FIG. 7.

In FIGS. 7 and 8, the sleeve 22 has a predetermined thickness 48. The body 32 and stripes 36 which make up the sleeve 22 have the same uniform thickness 48 through out the entire sleeve 22. Such an arrangement may be possible by forming the sleeve 22 directly via a coextrusion process, or by bonding uniformly thick pieces of alternating materials together. Other manufacturing methods, such as by selectively coating the sleeve with a material to form the stripe(s), which may be used to form the sleeve 22 shown may also be used.

Figure 9:
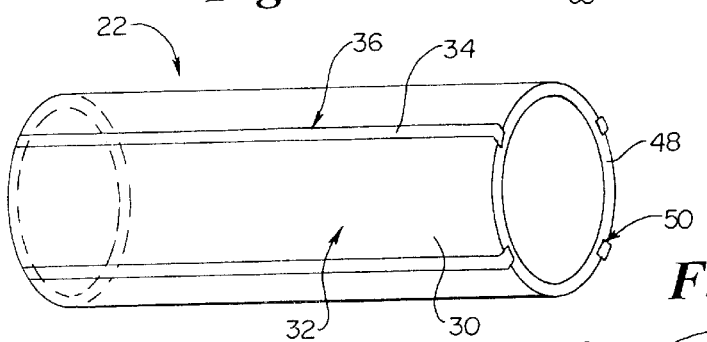
FIG. 9 is a perspective view of an embodiment of the invention.
Figure 10:
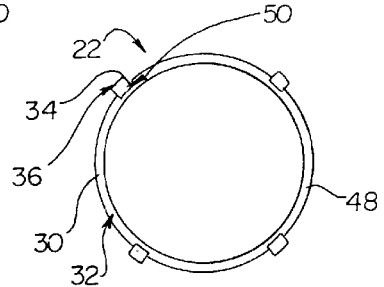
FIG. 10 is a cross-sectional view of the embodiment of the invention shown in FIG. 9.
Figure 11:
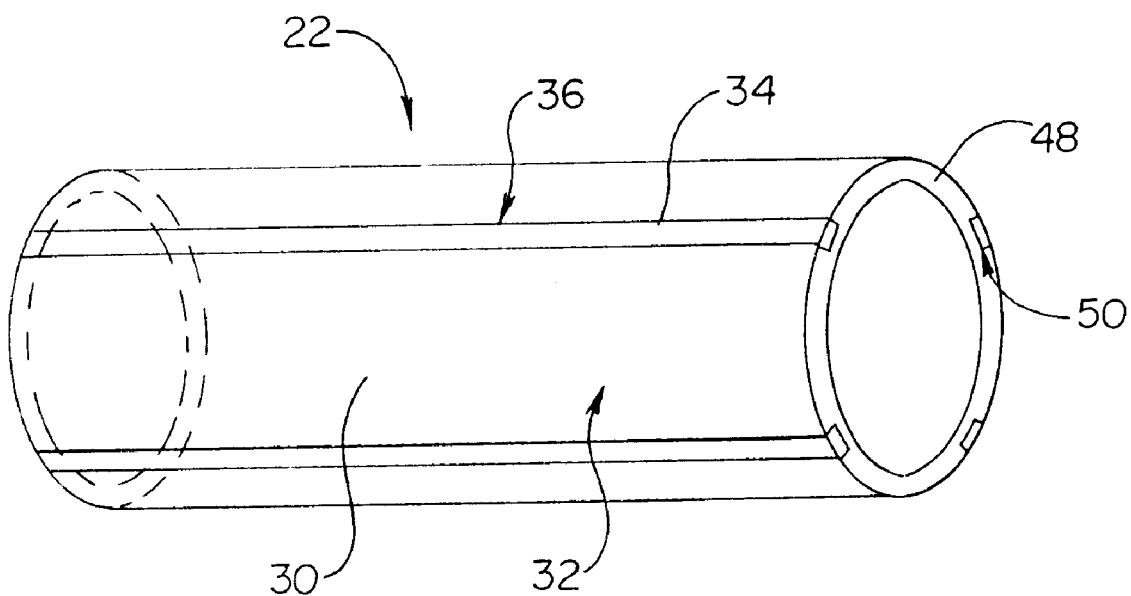
FIG. 11 is a perspective view of an embodiment of the invention.
Figure 12:
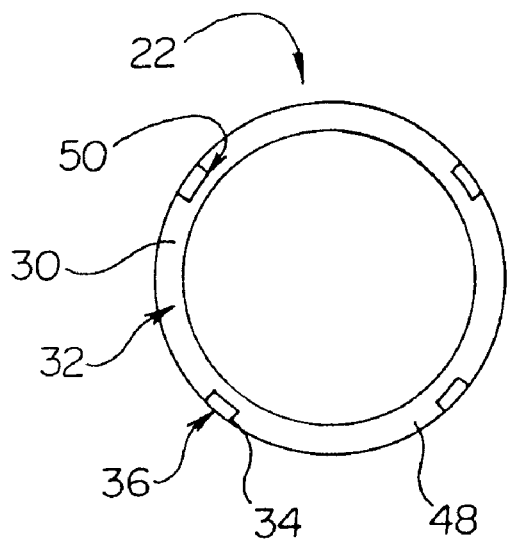
FIG. 12 is a cross-sectional view of the embodiment of the invention shown in FIG. 11.

In FIGS. 9 and 10 an embodiment of the sleeve 22 is shown wherein the stripes 36 are raised relative to the thickness 48 of the body 32. While the thickness of the 20 stripes 36 may be the same or different than that of the body 32, the stripes have a raised appearance because they are positioned in longitudinal grooves 50 positioned longitudinally about the circumference 40 of the sleeve 22. Such a 'raised stripe' may provide for stripe(s) of greater hardness which in turn provides for greater-sleeve stiffness. In the embodiment shown in FIGS. 11 and 12, the grooves 50 are also present but the stripes 36 are not raised thereby providing the entire sleeve 22 with a uniform thickness as well as a reduced profile relative to the stripe configurations shown in FIGS. 9 and 10.

In alternative embodiments, notably those utilized specifically for delivery of a self expanding stent, a retractable sheath (not shown) such as are known in the art, may be employed to overlay the stent. In such embodiments a single sleeve or two sleeves such have been shown and described may be employed to retain the self-expanding stent in place. When the sheath is retracted the stent will expand causing the sleeve(s) to retract.

In addition to being directed to the embodiments described above and claimed below, the present invention is further directed to embodiments having different combinations of the features described above and claimed below. As such, the invention is also directed to other embodiments having any other possible combination of the dependent features claimed below.

The above examples and disclosure are intended to be illustrative and not exhaustive. These examples and description will suggest many variations and alternatives to one of ordinary skill in this art. All these alternatives and variations are intended to be included within the scope of the attached claims. Those familiar with the art may recognize other equivalents to the specific embodiments described herein which equivalents are also intended to be encompassed by the claims attached hereto.

What is claimed is:

1. A stent delivery system comprising:
   a catheter including a stent mounting region;
   a stent disposed about the stent mounting region of the catheter, the stent having a distal end and a proximal end, the stent further having a unexpanded state and an expanded state, and
   at least one stent retaining sleeve, the at least one stent retaining sleeve having a first end and a second end, the first end overlying an end of the stent when the stent is in the unexpanded state, the second end engaged to at least a portion of the catheter adjacent to the stent mounting region, the at least one stent retaining sleeve comprising a first material and at least one substantially longitudinally oriented stripe of a second material, the first material having a predetermined hardness and the second material having a predetermined hardness, the predetermined hardness of the second material having a greater durometer value than the predetermined hardness of the first material.

2. The stent delivery system of claim 1, the at least one substantially longitudinally oriented stripe of a second material further comprising a plurality of substantially longitudinally oriented stripes.

3. The stent delivery system of claim 1, wherein the first material has a durometer hardness value in a range of approximately 40A to 100A, and the at least one substantially longitudinally oriented stripe of a second material has a durometer hardness value in a range of at least 40D to 75D.

4. The stent delivery system of claim 1 wherein the at least one substantially longitudinally oriented stripe of a second material further comprises a first portion and a second portion, the first portion having a first predetermined width, and the second portion having a second predetermined width, the first predetermined width being less than the second predetermined width, the first portion substantially oriented toward the first end of the at least one stent retaining sleeve and the second portion substantially oriented toward the second end of the at least one stent retaining sleeve, the first predetermined width tapering to the second predetermined width.

5. The stent delivery system of claim 4 wherein the first predetermined width is zero.

6. The stent delivery system of claim 1 wherein the at least one substantially longitudinally oriented stripe of a second material is intermittent.

7. The stent delivery system of claim 1 wherein the at least one substantially longitudinally oriented stripe of a second material is substantially sinusoidal in shape.

8. The stent delivery system of claim 1 wherein the at least one substantially longitudinally oriented stripe of a second material further comprising a predetermined patterned shape.

9. The stent delivery system of claim 1 wherein the first material and the at least one substantially longitudinally oriented stripe of a second material are co-extruded.

10. The stent delivery system of claim 1 wherein the at least one substantially longitudinally oriented stripe of a second material is a coating, the coating being applied to the first material of the at least one stent retaining sleeve.

11. The stent delivery system of claim 10 wherein the coating is selected from at least one member of the group consisting of: polyolefins, polystyrene, polyvinyl chloride, acrylonitrile-butadiene-styrene polymers, polyacrylonitrile, polyacrylate, vinyl acetate polymer, cellulose plastics, polyurethanes, polyethylene terephthalate, polyacetal, polyethers, polycarbonates, polyamides, polyphenylene sulfide, polyarylethersulfones, polyaryletherketones, polytetrafluoroethylene, and any combinations thereof.

12. The stent delivery system of claim 1, the at least one stent retaining sleeve having a predetermined thickness and the first material having at least one groove, the at least one groove having a predetermined thickness less than the predetermined thickness of the at least one stent retaining sleeve, at least one substantially longitudinally oriented stripe of a second material positioned within the at least one groove.

13. The stent delivery system of claim 1 wherein the first material has a predetermined thickness and the at least one substantially longitudinally oriented stripe of a second material has a predetermined thickness, wherein the predetermined thickness of the first material and the predetermined thickness of the at least one substantially longitudinally oriented stripe of a second material are the same.

14. The stent delivery system of claim 2, the at least one stent retaining sleeve further comprising a circumference, the plurality of substantially longitudinally oriented stripes being uniformly spaced apart about the circumference.

15. The stent delivery system of claim 1 wherein the first material is constructed from at least one member of the group consisting of: styrenic block copolymers, polyurethanes, silicone rubber, natural rubber, copolyesters, polyamides, EPDM rubber/polyolefin, nitril rubber/PVC, fluoroelastomers, butyl rubber, epichlorohydrin, and any combinations thereof.

16. The stent delivery system of claim 1 wherein the at least one substantially longitudinally oriented stripe of a second material is constructed from at least one member of the group consisting of: polyolefins, polystyrene, polyvinyl chloride, acrylonitrilebutadiene-styrene polymers, polyacrylonitrile, polyacrylate, vinyl acetate polymer, cellulose plastics, polyurethanes, polyethylene terephthalate, polyacetal, polyethers, polycarbonates, polyamides, polyphenylene sulfide, polyarylethersulfones, polyaryletherketones, polytetrafluoroethylene, and any combinations thereof.

17. The stent delivery catheter of claim 1, the first end of the at least one stent retaining sleeve having an unexpanded diameter and an expanded diameter, the expanded diameter of the first end being up to approximately 400 percent greater than the unexpanded diameter;

whereby when the stent is expanded from the unexpanded state to the expanded state the unexpanded diameter of the first end of the at least one stent retaining sleeve is increased by up to approximately 400 percent to the expanded diameter.

18. A stent retaining sleeve for retaining stent ends on a balloon catheter comprising:

a tubular member composed of a first material and at least one substantially longitudinally oriented stripe of a second material, wherein the first material has a predetermined hardness and the second material has a predetermined hardness, the predetermined hardness of the second material being greater than the predetermined hardness of the first material;

the tubular member having a first end and a second end, the first end constructed and arranged to overlay an end of a stent, the second end constructed and arranged to be in contact with at least a portion of said balloon catheter;

the first end of the tubular member having an unexpanded diameter and an expanded diameter whereby when the balloon catheter is expanded the unexpanded diameter increases by up to 400 percent to the expanded diameter.

19. The stent retaining sleeve of claim 18, the sleeve having an unexpanded length and an expanded length, the unexpanded length being substantially the same as the expanded length.

20. A stent delivery system comprising:

a catheter including a stent mounting region;

a stent disposed about the stent mounting region of the catheter, the stent having a distal end and a proximal end, the stent further having a unexpanded state and an expanded state, and at least one stent retaining sleeve, the at least one stent retaining sleeve having a first end and a second end, the first end overlying an end of the stent when the stent is in the unexpanded state, the second end engaged to at least a portion of the catheter adjacent to the stent mounting region, the at least one stent retaining sleeve comprising a first material and at least one substantially longitudinally oriented stripe of a second material, wherein the first material has a durometer hardness value in a range of approximately 40A to 100A, and the at least one substantially longitudinally oriented stripe of a second material has a durometer hardness value in a range of at least 40D to 75D.

\* \* \* \* \*